United States Patent [19]

Stutts et al.

[11] Patent Number: 4,488,944

[45] Date of Patent: Dec. 18, 1984

[54] ELECTROCATALYTIC OXIDATION OF (POLY)ALKYLENE GLYCOLS

[75] Inventors: Kenneth J. Stutts; Karel A. J. Snoble, both of Midland, Mich.

[73] Assignee: The Dow Chemical Company, Midland, Mich.

[21] Appl. No.: 543,199

[22] Filed: Oct. 19, 1983

[51] Int. Cl.$^3$ .................................................. C25B 3/02
[52] U.S. Cl. .................................... 204/79; 204/56 R
[58] Field of Search ............................... 204/79, 56 R

[56] References Cited

U.S. PATENT DOCUMENTS 3,725,290  4/1973  Nelson et al. .................. 252/110
3,929,873  12/1975  Gammans .................... 260/531 R
3,969,200  7/1976  Nohe et al. ........................ 204/79

FOREIGN PATENT DOCUMENTS 1051614  12/1966  United Kingdom ................. 204/78

OTHER PUBLICATIONS

J. Kaulen et al., *Synthesis* 513 (1979).
G. Vertes et al., *Tet.* 28, pp. 37-42 (1972).
M. Fleishmann et al., *J. Chem. Soc. Perkin II*, 1396, (1972).
G. Vertes et al., *Acta. Chem. Acad. Sci. Hung.*, 67 (1971).
M. Fleishmann et al., *J. Electroanal. Chem.* 31, 39 (1971).
P. M. Robertson, *J. Electrochem. Soc.*, 130 (3) (1983).

*Primary Examiner*—R. L. Andrews
*Attorney, Agent, or Firm*—Douglas N. Deline

[57] ABSTRACT

Dicarboxylic acids are prepared by oxidation of (poly-)alkylene glycols with electrochemically generated nickel-oxide hydroxide.

10 Claims, No Drawings

# ELECTROCATALYTIC OXIDATION OF (POLY)ALKYLENE GLYCOLS

BACKGROUND OF THE INVENTION

The present invention relates to a novel process for the preparation of dicarboxylic acids from (poly)alkylene glycols. More particularly, the present invention relates to the oxidation of (poly)alkylene glycols such as diethylene glycol employing electrochemically generated nickel-oxide hydroxide, NiO(OH).

It is already known to prepare carboxylic acids by chemical oxidation of (poly)alkylene glycols. For example, in U.S. Pat. No. 3,725,290 it was taught that nitric acid will oxidize diethylene glycol to diglycolic acid in high yield. Similarly in U.S. Pat. No. 3,929,873, a process for the heterogeneous platinum catalyzed air oxidation of (poly)ethylene glycols was disclosed. Certain strong chemical oxidants are unsuited for the oxidation of (poly)glycol ethers due to degradation of ether linkages or over-oxidation to the carbonate instead of the acid product.

Electrochemically prepared nickel (III) oxide hydroxide is already known to be suitable for the oxidation of primary alcohols. J. Kaulen et al. in *Synthesis*, 513 (1979), taught such an electrochemical oxidation of numerous aliphatic alcohols, including furfuryl alcohol, an aromatic ether, Ibid., at 514.

In GB No. 1,051,614, ethylene glycol, which contains no ether linkages, was oxidized by use of electrochemically prepared nickel-oxide hydroxide and a nickel anode. The product was glycolic acid.

G. Vertes et al., *Tet.* 28, 37–42 (1972), reported that no chemical difference could be detected between active nickel hydroxide prepared chemically and the active species formed on a nickel hydroxide electrode. Further research by the present inventors illustrated that chemically prepared NiO₂H, prepared by action of hydrogen peroxide on aqueous nickel salt solutions was not suitable in oxidizing ether alcohols, especially (poly)alkylene glycols. The products formed included unacceptable amounts of formates, carbonates and other over-oxidation or ether-cleavage products.

SUMMARY OF THE INVENTION

According to the present invention there is provided a process for preparing dicarboxylic acids corresponding to the formula:

wherein R' independently each occurrence is hydrogen, methyl or ethyl, and n is an integer from 0 to 10, comprising contacting a (poly)alkylene glycol corresponding to the formula:

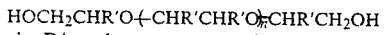

wherein R' and n are as previously defined, with electrochemically generated nickel-oxide hydroxide.

Surprisingly, the electrochemically generated nickel-oxide hydroxide employed in the present process does not substantially over-oxidize the (poly)alkylene glycol nor are ether linkages substantially affected by the oxidation.

The dicarboxylic acid products prepared by the invented process are useful chelating agents for use in synthetic detergent formulations. The products are also usefully employed as corrosion inhibitors and in the preparation of polymers, especially polyesters that are useful molding resins.

DETAILED DESCRIPTION OF THE INVENTION

The (poly)alkylene glycols for use in the present invention include the well-known (poly)ethylene glycols, i.e., compounds of the formula:

HOCH₂CH₂O(̶CH₂CH₂O)̶$_n$CH₂CH₂OH wherein n is an integer from 0 to 10. Also included are (poly)propylene or (poly)butylene glycols as well as mixed glycols of ethylene oxide, propylene oxide or butylene oxide.

Preferred (poly)alkylene glycol reactants are (poly)ethylene glycols. Most preferred is diethylene glycol that results in the corresponding commercial chelating agent, diglycolic acid.

The oxidation is accomplished by electrochemically generated nickel-oxide hydroxide, NiO(OH). Preferably, the nickel-oxide hydroxide is continuously regenerated by electric current during the oxidation process.

Several methods exist for the electrochemical generation of nickel-oxide hydroxide. One suitable process is Kandler deposition from a nickel salt solution. The process is described in several references including M. Fleischmann et al., *J. Chem. Soc. Perkin II*, 1396 (1972) or G. Vertes et al., *Acta Chem. Acad. Sci Hung.*, 67 (1971). Briefly, the nickel-oxide hydroxide is electrochemically formed as an active surface layer on an electrode by conversion of a previously deposited nickel (II) hydroxide layer.

According to one process, an electrode is immersed in an aqueous solution of a nickel salt and charged so as to cause the precipitation of nickel (II) hydroxide onto the electrode surface. Suitable nickel salts include nitrates, sulfates, etc. A preferred salt is nickel (II) nitrate. Additional counterions such as acetate are also present. Best results are obtained if the solution initially is modified by addition of hydroxide ion so as to be neutral or even slightly basic. Then upon application of an electric current nitrate ions are reduced to ammonia thereby quickly forming a basic solution around the electrode leading to precipitation of nickel hydroxide. A suitable aqueous solution comprises 0.1 N nickel salt, 0.1 M sodium acetate and 0.005 M sodium hydroxide. Preferred electrodes are metal electrodes, especially nickel or platinum. The electrode to be employed as the counter electrode may be iron, stainless steel, etc.

Multiple layers of nickel (II) hydroxide may be deposited, if desired, by alternately reversing the polarity of the two electrodes and recharging until sufficient nickel (II) hydroxide is deposited.

Once the nickel (II) hydroxide layer is prepared, it is converted to nickel-oxide hydroxide by contacting with hydroxide ion and applying electric potential of positive polarity. The resulting nickel-oxide hydroxide coating may alternatively be referred to as activated nickel hydroxide or nickel peroxide.

Nickel-oxide hydroxide prepared in the preceding manner is stable for several minutes or even hours. Upon contacting the nickel-oxide hydroxide with the (poly)alkylene glycol, the oxidation takes place and the desired dicarboxylic acid is prepared in high yields. The oxidation may take place neat, but preferably occurs in an aqueous electrolyte optionally containing a solvent such as an alcohol to aid in solubilizing the (poly)alkylene glycol and an alkali metal hydroxide. By passing a current through the electrolyte during the oxidation, the nickel-oxide hydroxide is continuously regenerated and serves to catalytically oxidize the (poly)alkylene glycol.

The above process for preparing nickel-oxide hydroxide could be employed in a commercial process, however, the inconvenience of preparing electrodes prior to the oxidation by using two separate treatment steps according to the Kandler process indicates that commercial application would be accomplished only with difficulty.

Accordingly, the present invented process employs as a preferred embodiment thereof the electrochemical generation of the nickel-oxide hydroxide oxidant in situ without use of the precipitation technique. The nickel-oxide hydroxide is prepared on a nickel anode by the technique of galvanostatic cycling. By the term galvanostatic cycling is meant that an electrical pulse train of first one polarity then the opposite polarity having a relatively constant current is applied to the nickel anode which is employed as part of an electrochemical cell. The process is to be distinguished from similar processes employing constant potential wave trains to anodes positioned similarly in an electrochemical cell. The process is described further hereinafter.

According to the process of galvanostatic cycling, an electrochemical cell having at least the anode comprised of nickel is contacted with an aqueous solution at basic pH. A preferred solution comprises hydroxide ions. Upon contact with the basic solution the nickel metal surface forms a coating of nickel (II) hydroxide. A constant current having a current density from about 5 mA/cm$^2$ of electrode surface to about 100 mA/cm$^2$ is pulsed through the cell for a short period on the order of few seconds. The polarity is then reversed for a similar period of time. The process is repeated for a time sufficient to prepare a desired thickness of nickel-oxide hydroxide. Charge densities greater than about 100 mA/cm$^2$ can lead to electrode damage while charge densities less than about 5 mA/cm$^2$ are insufficient to generate practical amounts of nickel-oxide hydroxide. During the positive polarization step as above described, the desired nickel hydroxide surface layer on the electrode is formed in one convenient step. Alternately reducing then reforming the nickel-oxide hydroxide surface layer has surprisingly been found to increase the physical strength and surface area of the deposited nickel-oxide hydroxide layer. The galvanostatic cycling ends with a final positive polarization to prepare the finished anode having a nickel-oxide hydroxide coating.

In the preferred embodiment, the current density during the galvanostatic cycling is from about 25 mA/cm$^2$ to about 50 mA/cm$^2$ and the nickel anode is positively charged for about 10 seconds, then reverse polarized for about 2 seconds. In the space of about 10 minutes, the above procedure produces a uniform coating of nickel-oxide hydroxide having a thickness on the order of about 100–150 monolayer equivalents. The nickel-oxide hydroxide prepared by the above technique provides an anode having better structural integrity than a corresponding anode prepared by electroprecipitation of metal salts (Kandler process). Compared to electroprecipitation processes, the instant technique is simplified and avoids contaminants often found in nickel salts.

In actual practice, the operator may employ two nickel electrodes in the present process and perform the galvanostatic cycling in the presence of both hydroxide ion and the (poly)alkylene glycol to be oxidized. In this manner, no pretreatment of the electrode other than cleaning in the usual manner need be performed, thereby greatly simplifying startup and preparation of the nickel-oxide hydroxide layer as well as regeneration of the nickel-oxide peroxide during operation. The presence of two nickel electrodes results in generation of substantially only the desired dicarboxylic acid products along with hydrogen and oxygen during the galvanostatic cycling process.

As previously mentioned, the galvanostatic cycling process requires the use of current densities well in excess of those associated with the active voltametric wave due to generation of nickel hydroxide. During the cycling process, the electrode is charged into the regions of oxygen and hydrogen evolution.

The oxidation of (poly)alkylene oxide is accomplished by contacting the above prepared nickel-oxide hydroxide deposited on a nickel anode with the (poly)alkylene glycol as previously described for electrodes prepared by the Kandler process. Preferably, the nickel-oxide hydroxide is employed catalytically and electrochemically reoxidized in situ as the (poly)alkylene glycol is consumed. For this purpose, the (poly)alkylene glycol is oxidized in the presence of hydroxide ion, preferably an alkali metal hydroxide and an electrical current is passed through the cell during the oxidation. During the oxidation the nickel-oxide hydroxide-containing electrode is anodically charged at a cell potential of from about 1.5 to about 3 volts depending on the cell configuration and electrolyte conductivity.

Once prepared according to Applicant'preferred galvanostatic cycling process (as opposed to the prior art techniques of precipitation with or without potentiostatic cycling), the electrode is stable and may be used for oxidation of the (poly)alkylene glycols with in situ reoxidation for extended periods of time, as long as 6 months or more of continuous use. When current efficiencies degrade to an unacceptable level, regeneration treatment by galvanostatic cycling of the nickel electrode in the previously described manner serves to restore the nickel-oxide hydroxide layer and the electrode efficiency.

When in operation the entire process results in the consumption of two moles of alkali metal hydroxide and eight faradays of electric current with the production of four moles of hydrogen for each mole of (poly)alkylene glycol oxidized to the corresponding dicarboxylic acid disalt.

The cell for use in the present process is of ordinary design and construction. Suitable cells may be undivided or divided by means of a permeable membrane between the anode and cathode. The desired dicarboxylic acid is obtained in the alkali metal salt form. According to a continuous process, the diglycolic acid salt may be precipitated in a settling tank as its solubility limit is reached and conveniently separated by filtration. Solubilizing agents such as tertiary alcohols or inorganic salts may be employed in order to reduce the solubility of the acid salt thereby aiding in its recovery.

SPECIFIC EMBODIMENTS

Having described the invention, the following examples are provided as further enabling and are not to be construed as limiting the invention to the specific embodiments depicted.

EXAMPLE 1

Preparation of diglycolic acid

Stainless steel (S.S. 304, 40-mesh) electrodes with geometric areas of 26 cm$^2$ and 84 cm$^2$ are used as working and counter electrodes, respectively. Pretreatment involves a precautionary cleaning by immersion in aqua regia for about 5 seconds and thorough rinsing with distilled water. The electrodes are then placed in an undivided electrochemical cell which contains 0.3 M NiNO$_3$ (pH about 2.6), and a constant current (65 mA) is passed for 300 seconds with the working electrode polarized cathodically. Electrodeposition of Ni(OH)$_2$ is accomplished by discharge of NO$_3^-$ forming ammonia and water. The pH near the electrode surface increases and precipitation of nickel as the hydroxide occurs. The electrodes are then thoroughly rinsed, immersed in 2 M NaOH and polarized galvanostatically at a current of 65 mA for 300 seconds such that the working electrode is the anode. A black coating appears on the working electrode, evidencing the formation of NiO(OH). The electrodes are rinsed again, and immersed in 40 ml of 2 M NaOH.

Potentiostatic application of +0.450 V vs. Ag/AgCl (saturated KCl) to the pretreated working electrode results in a current (transient) which decays rapidly to less than 10 mA in the stirred solution. Addition of 2.2377 g of diethylene glycol results in an increase in current to about 0.2 A. The electrolysis is allowed to proceed for 64.5 hours after which 18,820 Coulombs are passed (116 percent of the theoretical charge of 8e$^-$ moles$^{-1}$). Liquid chromatographic analysis indicates an 88 percent yield of diglycolic acid at a current efficiency of 76 percent.

EXAMPLE 2

A platinum working electrode (26 cm$^2$) and stainless steel counter electrode are pretreated as in Example 1. Galvanostatic electrolysis of 2.2722 g of diethylene glycol at 0.26 A is allowed to proceed until 21,140 Coulombs (128 percent of the theoretical charge) have passed. Liquid chromatographic analysis indicates an 83 percent yield of diglycolic acid with a 65 percent current efficiency.

EXAMPLE 3

An X-met nickel working electrode (34 cm$^2$) and a stainless steel counter electrode are cleaned in aqua regia, rinsed, and then immersed in a solution which contains 0.1 M NiSO$_4$, 0.1 M NaCH$_3$COO and 0.01 M NaOH. Galvanostatic pretreatment at 17 mA for 60 seconds is performed with the working electrode as anode, then the polarity is reversed for 60 seconds. This galvanostatic procedure is repeated 6 times. Finally, 17 mA is passed for 120 seconds with the working electrode as anode, which results in a fine black coating. The electrodes are rinsed with H$_2$O, and then immersed in 40 ml of 10 N NaOH containing 2.0591 g of diethylene glycol.

Potentiostatic electrolysis (+0.270 V vs. Ag/AgCl (saturated KCl)) results in a 75 percent yield of diglycolic acid (determined by liquid chromatography) at a 60 percent current efficiency. Neutralization of the reaction-product mixture with H$_2$SO$_4$, rotoevaporation, and drying under vacuum for 2 hours results in a white solid. This solid is transferred to a Soxhlet thimble and extracted with methanol for 17 hours. A white solid precipitates in the Soxhlet receiver. Rotoevaporation of the methanol and drying under vacuum at 85° C. for 2½ hours yields 2.635 g of solid diglycolic acid. Yield 71 percent, 92.4 percent purity.

EXAMPLE 4

Nickel X-met (87 cm$^2$) is separated from a stainless steel (304, about 90 cm$^2$) auxiliary electrode with polypropylene netting. This electrode system is cleaned in nitric acid and then rinsed with deionized water. After immersion in 2 M NaOH, a constant current of 2 amps is passed for 10 seconds with the Ni X-met polarized positively. The polarization is then switched for 2 seconds. Application of this pulse train for 10 minutes results in definite chromatic alterations. Subsequently, a 5-minute positive polarization of the Ni X-met at 2 A results in a uniform black coating. The electrodes are disconnected from the galvanostat, washed with dionized water, and then immersed in 200 ml of 2 M NaOH. Diethylene glycol (0.154 mole) is added to the solution with stirring after the Ni X-met is polarized positively at 2 A. At 111,400 Coulombs and 124,300 Coulombs, 10 ml of 5 M NaOH is added. The electrolysis is stopped at 130,400 Coulombs. The yield of diglycolic acid (via liquid chromatography) is 78 percent, with a current efficiency of 71 percent. No discernible diethylene glycol remains.

What is claimed is:

1. A process for preparing dicarboxylic acids corresponding to the formula:

wherein R' independently each occurrence is hydrogen, methyl or ethyl, and n is an integer from 0 to 10, comprising contacting a (poly)alkylene glycol corresponding to the formula:

wherein R' and n are as previously defined, with electrochemically generated nickel-oxide hydroxide.

2. A process according to claim 1 wherein the (poly)alkylene glycol is a (poly)ethylene glycol.

3. A process according to claim 2 wherein the (poly)ethylene glycol is diethylene glycol.

4. A process according to claim 1 wherein the electrochemically generated nickel-oxide hydroxide is continuously reoxidized by electrolyzing an electrochemical cell comprising:
   (1) an anode having a surface coating of nickel-oxide hydroxide;
   (2) a cathode; and
   (3) an aqueous electrolytic solution comprising the (poly)alkylene glycol and an alkali metal hydroxide.

5. A process according to claim 4 wherein the anode comprises nickel or platinum having a surface coating of nickel-oxide hydroxide.

6. A process according to claim 5 wherein the surface coating of nickel-oxide hydroxide is prepared by electrochemically oxidizing a surface layer comprising nickel (II) hydroxide in an aqueous alkali metal hydroxide solution.

7. A process according to claim 6 wherein the surface layer comprising nickel (II) hydroxide is prepared by Kandler deposition.

8. A process according to claim 6 wherein the anode comprises nickel metal.

9. A process according to claim 4 wherein the anode comprises nickel metal.

10. A process according to claim 9 wherein the surface coating of nickel-oxide hydroxide is prepared by galvanostatic cycling of the anode in a basic aqueous solution.

* * * * *